US010568649B2

(12) United States Patent
Roger (10) Patent No.: US 10,568,649 B2
(45) Date of Patent: Feb. 25, 2020

(54) ACETABULAR REAMER (71) Applicant: Howmedica Osteonics Corp., Mahwah, NJ (US)

(72) Inventor: Christopher Abee Roger, Waldwick, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1239 days.

(21) Appl. No.: 14/270,642

(22) Filed: May 6, 2014

(65) Prior Publication Data

US 2015/0320428 A1 Nov. 12, 2015

(51) Int. Cl.
*A61B 17/17* (2006.01)
*A61B 17/16* (2006.01)
*A61B 17/00* (2006.01)
*A61B 17/56* (2006.01)

(52) U.S. Cl.
CPC ...... *A61B 17/1746* (2013.01); *A61B 17/1666* (2013.01); *A61B 17/1617* (2013.01); *A61B 17/56* (2013.01); *A61B 2017/0042* (2013.01)

(58) Field of Classification Search
CPC ............ A61B 17/1631; A61B 17/1633; A61B 17/1664; A61B 17/1746; A61B 17/1666; A61B 2017/320032; A61B 19/26; A61B 17/1617; A61B 17/56; A61B 2017/0042
USPC .... 606/80, 87, 89, 79, 104, 180, 85, 99, 62, 606/88, 91, 53
See application file for complete search history.

(56) References Cited

U.S. PATENT DOCUMENTS

| 3,423,068 | A | | 1/1969 | Hall | |
| 3,835,858 | A | * | 9/1974 | Hagen | A61B 17/1633 408/141 |
| 4,071,029 | A | | 1/1978 | Richmond et al. | |
| 4,245,985 | A | * | 1/1981 | Eibofner | A61C 1/185 433/105 |
| 4,305,394 | A | | 12/1981 | Bertuch, Jr. | |

(Continued)

FOREIGN PATENT DOCUMENTS

| EP | 0189807 A2 | 8/1986 |
| EP | 2626017 A1 | 8/2013 |
| WO | 2005044153 A1 | 5/2005 |

OTHER PUBLICATIONS

Lauener Medical Devices—Porte Fraise, http://www.lauenermedical.ch/fr/instruments/angle-reamer-handle.html, pp. 1-2, printed Nov. 11, 2013.

(Continued)

*Primary Examiner* — David W Bates
*Assistant Examiner* — Marcela I Shirsat
(74) *Attorney, Agent, or Firm* — Lerner, David, Littenberg, Krumholz & Mentlik, LLP (57) ABSTRACT An acetabular reamer has a rotatable drive shaft extending along a first longitudinal central axis. A second housing surrounds at least a portion of the drive shaft, the first housing having a gripping arm. A drive motor in a first housing is coupled to a first end of the rotatable drive shaft for rotating the drive shaft. A reamer head is rotatably coupled to a second end of the rotatable drive shaft, the reamer head rotatable about a second axis extending at an acute angle with respect to the rotatable drive shaft first longitudinal. A releasable connector couples the first and second housing and prevent relative rotation between the first housing and the second housing.

23 Claims, 11 Drawing Sheets

(56) References Cited

U.S. PATENT DOCUMENTS

| | | | |
|---|---|---|---|
| 4,382,790 A * | 5/1983 | Loge | A61C 1/18 |
| | | | 433/126 |
| 4,475,549 A | 10/1984 | Oh | |
| 4,632,111 A | 12/1986 | Roche | |
| 5,037,424 A | 8/1991 | Aboczsky | |
| 5,061,270 A | 10/1991 | Aboczky | |
| 5,160,263 A * | 11/1992 | Meller | A61C 17/005 |
| | | | 433/125 |
| RE34,556 E | 3/1994 | Sjostrom et al. | |
| 5,320,625 A | 6/1994 | Bertin | |
| 5,658,290 A | 8/1997 | Lechot | |
| 6,395,005 B1 | 5/2002 | Lovell | |
| 6,423,070 B1 | 7/2002 | Zeppelin | |
| 6,500,169 B1 | 12/2002 | Deng | |
| 6,702,760 B2 | 3/2004 | Krause et al. | |
| 7,335,207 B1 | 2/2008 | Smith | |
| 7,803,160 B2 | 9/2010 | Keller | |
| 8,282,639 B2 | 10/2012 | Chana | |
| 8,348,959 B2 | 1/2013 | Wolford et al. | |
| 8,480,674 B1 | 7/2013 | Roger et al. | |
| 8,523,845 B2 | 9/2013 | Ippisch | |
| 2003/0229356 A1 | 12/2003 | Dye | |
| 2004/0172036 A1 | 9/2004 | Dye | |
| 2005/0124981 A1 | 6/2005 | Desarzens et al. | |
| 2007/0293869 A1 * | 12/2007 | Conte | A61B 17/1617 |
| | | | 606/91 |
| 2008/0021481 A1 | 1/2008 | Burgi | |
| 2008/0065081 A1 | 3/2008 | Lechot et al. | |
| 2009/0240256 A1 | 9/2009 | Smith | |
| 2012/0136360 A1 | 5/2012 | Aux Epaules et al. | |
| 2012/0136361 A1 | 5/2012 | Aux Epaules et al. | |
| 2013/0053904 A1 | 2/2013 | Penenberg | |

OTHER PUBLICATIONS

"How dental drill is made—material, making, history, used, processing, parts, components, composition, structure", Website: <http://www.madehow.com/Volume-3/Dental-Drill.html>, Nov. 15, 2013, 5 pages.

Ridgid, "JobMax 18V Multi-Tool with Tool-Free Head Bare Tool", <http://www.ispot.tv/ad/7bLN/the-home-depot-ridgid-jobmax>, Dec. 4, 2013, 8 pages.

Symmetry medical brochure, "Variable Angle Acetabular Reamer Drive", Jan. 2010, 1 page.

The Home Depot, "Drill 90 Right Angle Drill Attachment—1390/100507163", Website: <http://www.homedepot.com/p/Milescraft-Drill90-Right-Angle-Drill-Attachment-1390/100507163?cm_sp=BazVoice-_-RLP-_-100507163-_-x>, Nov. 15, 2013, 3 pages.

* cited by examiner

ACETABULAR REAMER

BACKGROUND OF THE INVENTION

The present invention is directed to implantation of artificial joint components and in particular to acetabular joint components. More particularly, it relates to an instrument for reaming the acetabular socket which allows the connection of and removal of acetabular reamer cutting heads and the application of force to the reamer head mounted on an angled reamer housing. While the instrument is described in connection with an acetabular reamer, it should be noted that the reamer disclosed can be used with other joints. In the case of a reamer, there is typically a drive shaft located within the instrument housing for rotating the reamer cutting head.

Total hip replacement or arthroplasty operations have been performed to repair the acetabulum and the region surrounding it and to replace the hip components such as the natural femoral head and acetabular socket which have degenerated.

With regard to the acetabulum, many instruments have been designed to locate either the acetabular cup or provide reamers for repairing the acetabulum to receive such a prosthetic cup. Such instruments are shown in U.S. Pat. Nos. 4,305,394, 4,632,111, 5,037,424, 5,061,270, 5,320,625, and 6,395,005.

In addition, there have been various designs for the acetabular reamers themselves, including the reamer and holder shown in U.S. Pat. No. 5,658,290. A similar reamer is shown in U.S. Publication No. 2005/0124981 along with a holder for the same. While these patents show holders for mounting the reamer via a drive shaft to a power source, it has been found that an improved force application system that reduces torque applied to the reamer head and handle from the motor driving the drive shaft for the reamer head is desirable.

In general, such instruments include a shank or handle portion which has a hollow housing which houses a rotatable drive system. The handle housing leading end includes a quick disconnect for coupling, for example, an acetabular cutting reamer having a hemispherical cutting surface and a coupling system on the acetabular reamer preferably having four rods, bars, or other coupling elements extending from a central hub area preferably located adjacent the equator of the hemispherical cutting surface. Of course the hub could be eliminated with the bars extending continuously across the reamer and the rods or bars could be recessed within the reamer cavity.

Generally orthopedic reaming, including acetabular reaming, utilizes a series of reamers which increase in size in one or two millimeter steps. These reamers are used in series to enlarge an opening for the receipt of a prosthetic implantation. Incremental reamers are required because excessive heat is generated if the surgeon tries to remove too much tissue or bone with a single reamer. In addition, surgeons may wish to remove the reamer either in the wound or outside thereof to verify the size, bone condition, and implant orientation. Because of this the surgeon must be able to connect and disconnect the reaming tool from the holder preferably in a simple, easy step, and replace a first reamer with a second reamer positively and quickly.

Currently, acetabular reamers such as shown in U.S. Patent Publication No. 2004/0172036 and U.S. Pat. Nos. 8,282,639 and 8,348,959 show reamer handles having a connector at the end opposite the reaming head which connector is adapted to connect to a drive motor. The drive motor may be an electric motor or a pneumatic motor. It can be seen with the above reamers that one must hold the drive motor and the handle drive system or housing of the acetabular reamer to prevent relative rotation therebetween. This requires the surgeon use both hands to prevent relative rotation between the motor and housing when reaming the acetabulum.

BRIEF SUMMARY OF THE INVENTION

It has been found to advantageous to provide a drive connection which allows the surgeon to actuate the motor via a trigger-type switch, while allowing the surgeon to have one hand free during the acetabular reaming operation for applying a force along the axis of rotation of the reamer cutting head. This can be accomplished by rigidly fixing the drive motor, for example, housed in a first cylindrical or pistol-type gripping housing to a second housing which houses the drive shaft for the acetabular reamer. The first housing also includes a trigger or switch for actuating an output connector in the motor. The rigid connection preferably is releasable and has inter-engaging structures which prevent the relative rotation between the first housing which houses the drive motor and trigger switch with the second housing including the drive shaft for the reamer head. This is especially advantageous if the reamer housing is an angled reamer housing, in which the axis of the reamer head which is used to prepare the acetabulaum is at an angle with the axis of the drive shaft and the motor output axis.

It has been found to be especially advantageous to allow the surgeon to use the free hand to apply pressure along the angled axis of the reamer cutting head. This can be accomplished by using a modular handle engagable at different locations along the second housing which houses the drive system extending along a drive axes of the motor output and power transmission shaft located within a straight portion of the acetabular reamer second housing. It has been found especially advantageous to utilize several locations along the reamer housing for a modular attachment of a handle to the shaft to accommodate for various anatomic differences. The several different locations all allow the surgeon to apply pressure via the handle mounted on the second housing parallel to or coaxially with the axis of rotation of the reamer cutting head during preparation of the acetabulum.

These and other aspects of the invention may be accomplished by an acetabular reamer a first housing including a drive motor and a second housing having a rotatable drive shaft extending along a first longitudinal central axis, the drive shaft having first and second ends. The second housing surrounds at least a portion of the drive shaft, the second housing having a gripping portion. The drive motor having an output shaft located in the first housing operatively coupled to the first end of the rotatable drive shaft for rotating the shaft located within the second housing. A reamer head rotatably is coupled to the second end of the rotatable drive shaft, the reamer head rotatable about a second axis extending in a first direction at an acute angle with respect to the rotatable drive shaft first longitudinal central axis. A first releasable connector operatively couples the first end of the rotatable drive shaft and the drive motor. A second releasable connector prevents relative rotation between the first housing and the second housing. A third releasable connector couples the second portion of the drive shaft and the reamer head.

The second housing preferably encloses the entire rotatable drive shaft. The drive motor is connected to the drive shaft and is non-rotatably mounted in the first housing. The gripping portion of the second housing enclosing the drive system includes a mounting connector for coupling an arm extending therefrom at the acute angle in a second direction generally opposite the first direction.

The arm is modular and may be releasably coupled and uncoupled from the second housing. The second housing has at least two and preferably three axially spaced connector locations for receiving the modular arm. A second connector location is spaced axially along the second housing at a greater distance from the reamer head than the first location. The acute angle between the drive system axis and the arm axis is about 45°.

The second housing having the drive shaft has a first axially extending portion with a first longitudinal axis and a second axially extending portion with a second longitudinal axis, the first and second longitudinal axis intersecting at the acute angle. The first and second axially extending portions of the drive shaft are releasable preferably connected by a universal joint coupling the rotatable drive shaft extending along the first longitudinal axis to the reamer head drive shaft extending along the second longitudinal axis. The drive motor may be either electric or pneumatic. The acute angle is about 45° between the drive shaft first portion connected to the motor and the axis of rotation of the reamer cutting head as well as between the modular arm and the axis of the drive shaft first portion. This allows the surgeon to transmit force in the direction of the reamer head axis of the rotation by applying pressure to the arm.

Various aspects of the invention are also provided by an acetabular reamer having a first housing containing a drive motor system having an output shaft therein extending out of the first housing along a first axis. A reamer portion has a second housing having a reamer drive shaft therein. The second housing having a first end housing a first end of the reamer drive shaft for connection to the drive motor system. The reamer drive shaft has a second end operatively coupled to an acetabular reamer cutting head. The first and second housings have interlocking portions for coupling the drive motor system to the reamer cutting head drive shaft and for preventing relative rotation between the first and second housings. The reamer drive shaft and the output shaft interlocking portions capable of transferring power from the motor output shaft to the reamer drive shaft.

The first housing preferably encloses the entire rotatable drive shaft. The drive motor system comprises a drive motor connected to the drive shaft, the drive motor being mounted in the first housing. The first end of the reamer drive shaft extends in a first direction forming an acute angle with respect to the second end of the reamer drive shaft coupled to the acetabular reamer cutting head.

The first housing may include a gripping portion formed adjacent the first end of the reamer drive shaft and includes a modular gripping handle having an arm extending from the second housing at the acute angle in a second direction opposite the first direction. This allows the surgeon to apply force along the reamer cutting head axis. The gripping arm is modular and may be releasably coupled to the second housing. The second housing has at least two, and preferably three axially spaced locations for receiving the modular arm. The second location is spaced axially along the second housing at a greater distance from the acetabular reamer cutting head than the first location. The acute angle is about 45°.

The reamer drive shaft has a first axially extending portion with a first longitudinal axis and a second axially extending portion with a second longitudinal axis, the first and second longitudinal axis intersecting at an acute angle of preferably about 45°. A connector including a universal joint may couple the reamer drive shaft first axially extending portion to the second axially extending portion which drives the reamer cutting head at an angle of about 45° to the drive system axis in the first portion of the second housing. The motor output shaft is preferably coaxial with the longitudinal axis in the first axially extending portion of the drive shaft. The drive motor may be either electric or pneumatic.

DETAILED DESCRIPTION

Figure 1:
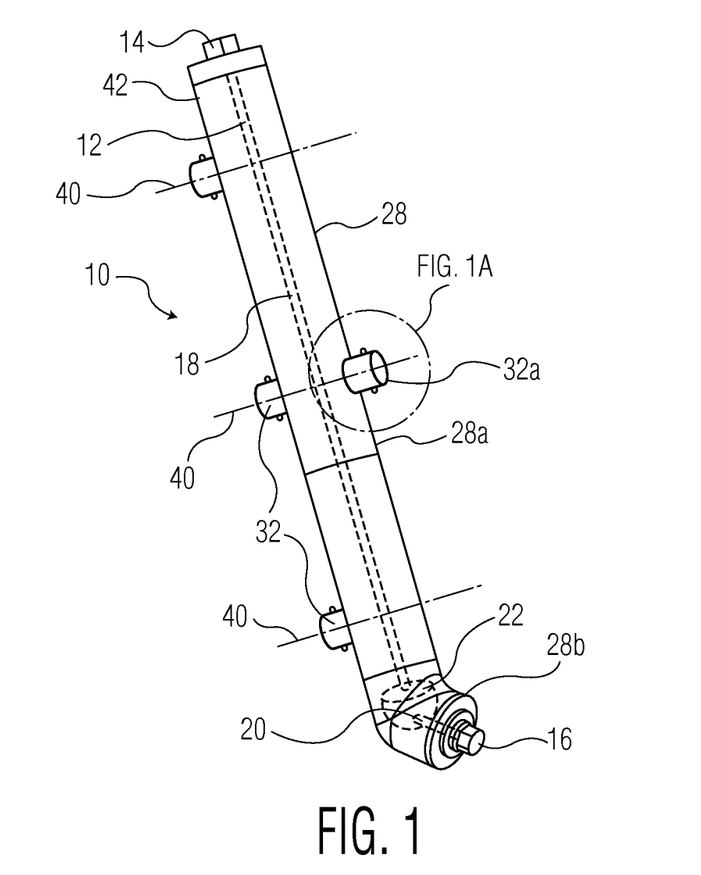
FIG. 1 is an isometric view of a reamer drive portion including an angled drive shaft for powering the cutting head of an acetabular reamer.
Figure 2:
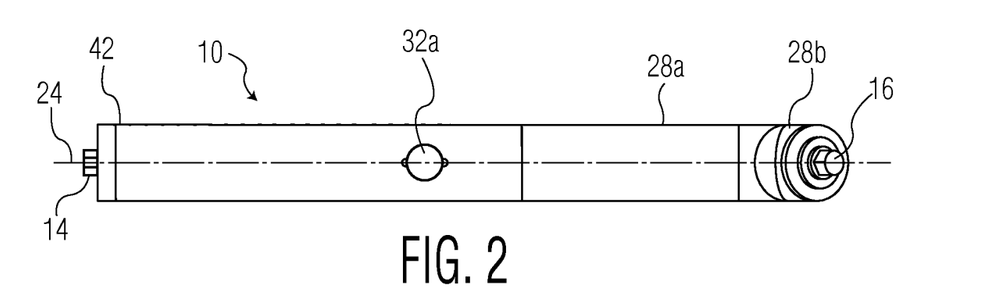
FIG. 2 is a top view of acetabular reamer drive housing of FIG. 1.
Figure 3:
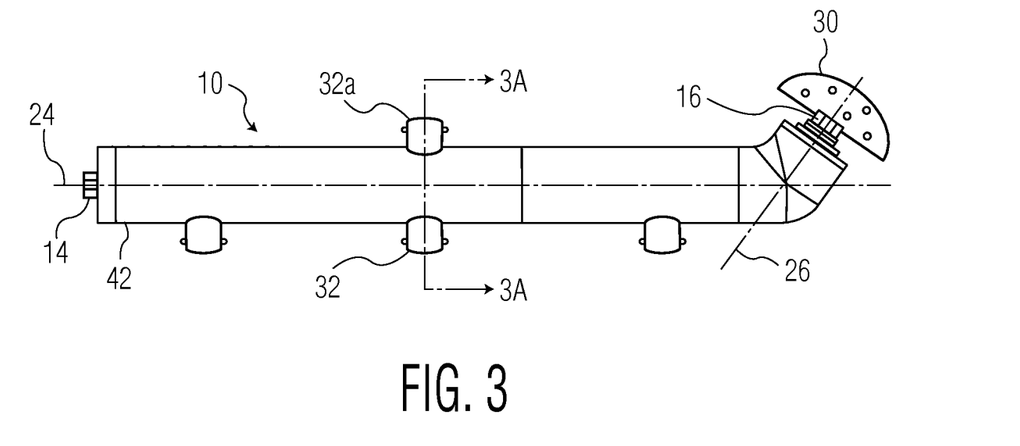
FIG. 3 is an elevation view of the drive housing of FIG. 1.

Referring to FIGS. 1-3, there is shown an instrument generally denoted as 10, which has a housing 28 which houses a drive system having a drive shaft 12 shown in phantom. Drive shaft 12 includes an input element 14 which may be a solid hex-shaped drive element and an output element 16 which is also preferably a hex-drive element. Input element 14 connects to a typical power tool. These drive elements are well known. Preferably drive shaft 12 includes a preferably straight first portion 18 and a second portion 20 connected by a U-joint 22. U-joint 22 is required since in the preferred embodiment the axis of rotation of hex-drive input 14 and first portion 18 is along an axis 24 and the output element 16 and portion 20 extends along an axis 26, which axes are at an angle to one another as shown in FIG. 3. The angular offset may be anywhere between 30 and 60° and preferably about 45°.

Drive shaft 12 is preferably surrounded by a cylindrical metal housing 28 which has a straight first portion 28a surrounding the straight portion 18 of drive shaft 12 and a second portion 28b surrounding drive shaft portion 20 which shaft portion drives output element 16. Referring to FIG. 3, it can be seen that output element 16 couples to and drives an acetabular reaming head 30 which can be of any standard design. Furthermore output element 16 can be of any design typically used to drive acetabular reamers.

Figure 1A:
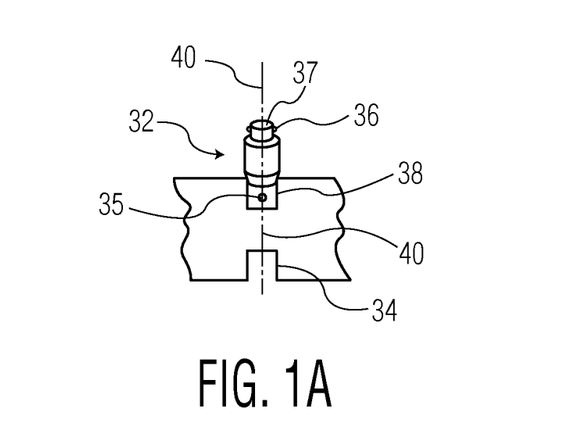
FIG. 1A shows a releasable connector element for use with the reamer drive portion of FIG. 1.

Again referring to FIGS. 1-3, there is shown a multiplicity of handle attachment points in the form of connectors 32, which connectors are releasably mounted on housing 28a. Connector 32 is shown in FIG. 1A and may be releasably mounted in preferably three recesses 34 spaced along shaft portion 28a. Connector 32 may include a first pair of spring-loaded ball detents 35 mounted on opposite sides of square extension 38 for holding connector 32 in recesses 34 formed in housing 28 or housing portion 28a and may include a second pair of ball detents 36 on a boss 37 to releasably mount a modular handle as described below. The ball detents 35, 36 can be located on opposite sides of extension portion 38 to provide sufficient force to maintain the connector in recess 34.

Preferably, three recesses 34 are provided on one side of housing portion 28a and each recess 34 has a central axis 40 located in a plane containing both longitudinal axis 24 and longitudinal axis 26. This allows any forces applied to central axis 40 of connector 32 to act along the plane containing axes 24 and 26. A fourth connector 32a is mounted on a side of housing 28a opposite, preferably 180°, from the side with the three connectors 32. Again the central axis 40 of the fourth connector 32a lies in the same plane as the first three connectors 32 and is preferably coaxial with the axis of the central connector 32.

Figure 3A:
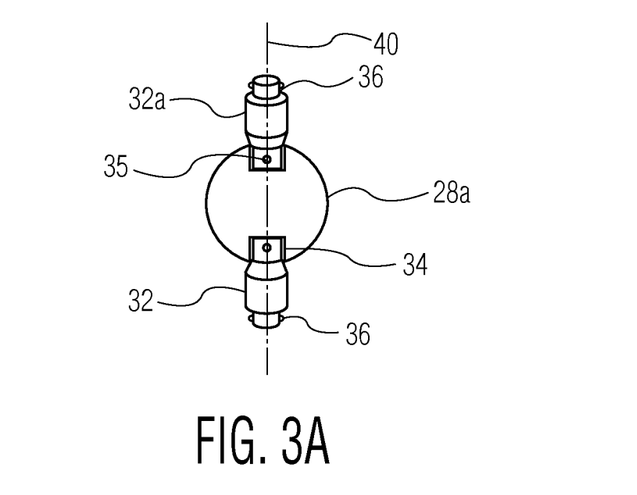
FIG. 3A is a partial cross-sectional view of FIG. 3 along lines 3A-3A showing the connector of FIG. 1A on the drive portion of FIG. 1.

Referring to FIG. 3A there is shown a cross-sectional view through a pair of connectors 32 coaxially mounted on opposite sides housing portion 28a. Thus as shown in FIGS. 1-3, a modular handle can be connected to housing portion 28a at three coplanar locations on a first side whose central axes 40 all lie in a plane containing axes 24 and 26 to allow movement of instrument 10 in a direction of axis 26 when reaming an acetabulum. Connector 32a on the opposite side can be used to attach a handle adapted to allow the instrument 10 to be manipulated in an alternate direction.

Figure 4:
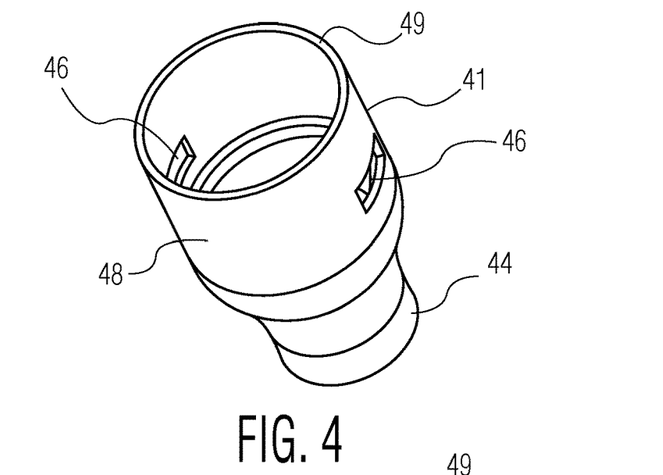
FIG. 4 is an isometric view of a sleeve connector sleeve which may be fixed to an input drive end of the drive portion of FIGS. 1-3.
Figure 5:
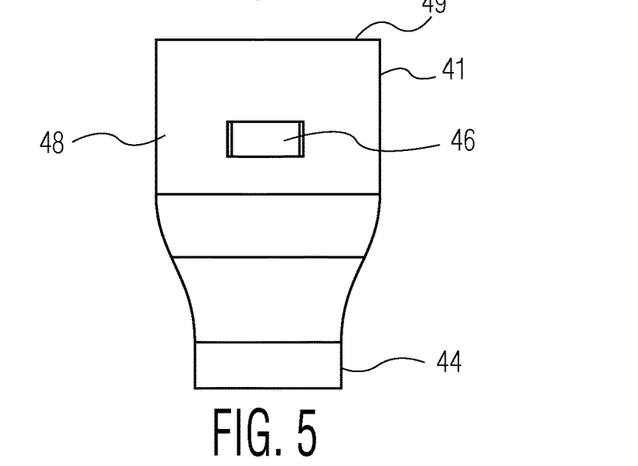
FIG. 5 is an elevation view of the sleeve of FIG. 4.
Figure 6:
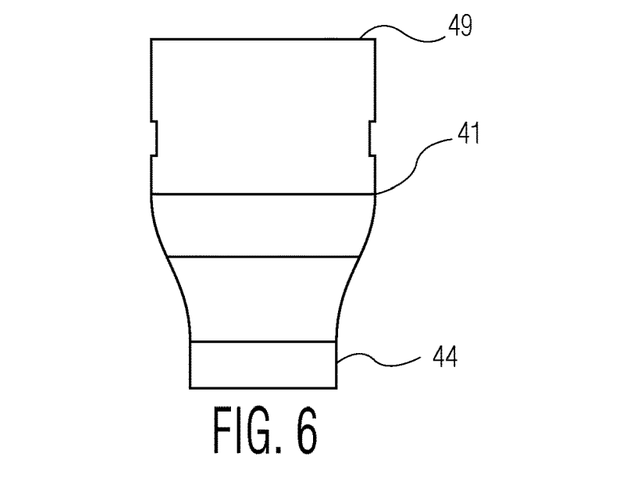
FIG. 6 is an elevation view of the sleeve of FIG. 4 rotated 90° with respect to the elevation view shown in FIG. 5.
Figure 7:
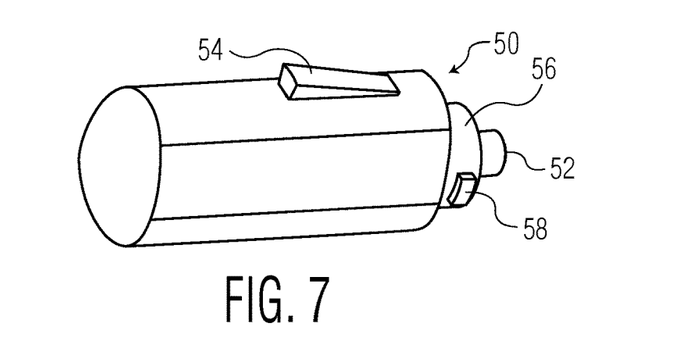
FIG. 7 is an isometric view of a drive motor housing including an actuator switch which housing is adapted to connect to the wide end of the sleeve of FIG. 4.
Figure 8:
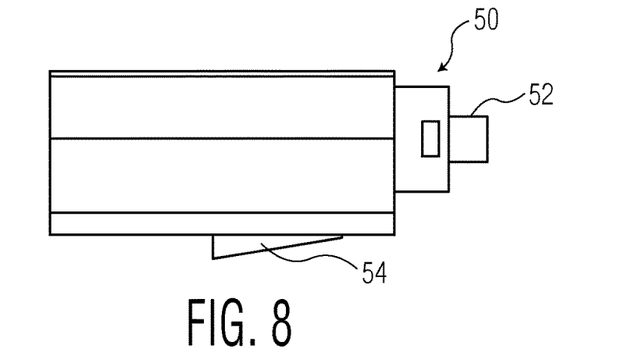
FIG. 8 is an elevation view of the drive motor housing of FIG. 8.
Figure 9:
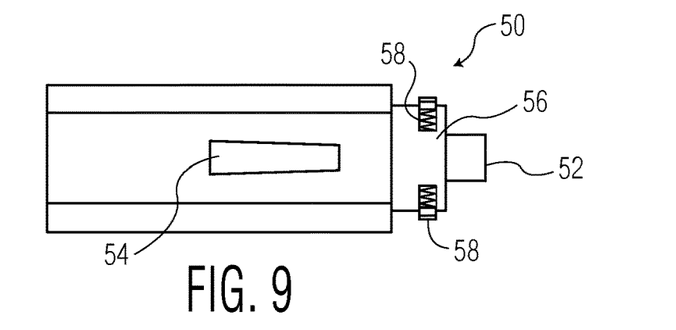
FIG. 9 is an elevation view of the drive motor housing of FIG. 7 rotated 90° from the view of FIG. 8.
Figure 10:
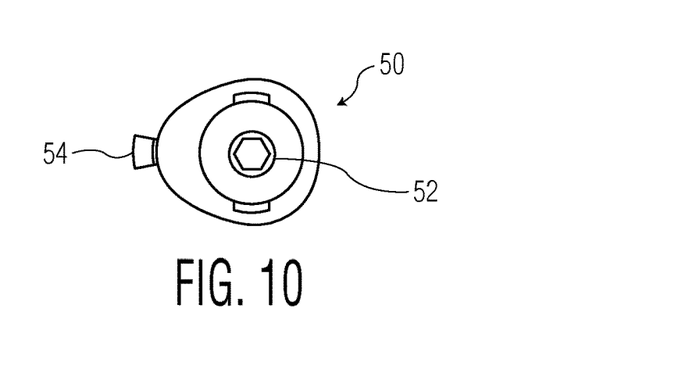
FIG. 10 is an end view of the drive motor housing of FIG. 9, when viewed from the right-hand side.

Referring to FIGS. 4-6, there is shown a coupling sleeve 41 which can be either fixedly or modularly attached to an end 42 of housing 28. End 44 of sleeve 41 thus can be fixedly connected such as by welding or press-fitting onto end 42 of housing 28. Alternatively there can be a bayonet type coupling (not shown) which would allow easy removal of sleeve 41. Sleeve 41 includes a pair of slots or openings 46 extending through hollow cylindrical wall 48 which forms an enlarged end of sleeve 41. Sleeve 41 has an open end 49 adapted to receive a drive motor housing as shown in FIGS. 7-10.

Referring to FIGS. 7-10 there is shown a housing generally denoted as 50 for housing a drive motor (not shown) which includes a female hex socket output shaft 52 sized to receive the hex input element 14 of the drive shaft 12. If electric, the drive motor may be driven by a battery housed in housing 50 or may be connected via a power cord. Any actuator for the drive motor may be used such as a switch 54 shown in FIGS. 7-10 which may either be an on/off switch or a switch allowing variable output speeds. Housing 50 includes a leading end 56 which includes a pair of spring detent elements 58 which are adapted to snap into openings 46 of sleeve 41. Detents 58 may have beveled leading and trailing surfaces to aid in compression upon insertion or removal of drive system housing 50 into and out of end 49 sleeve 41.

Figure 11:
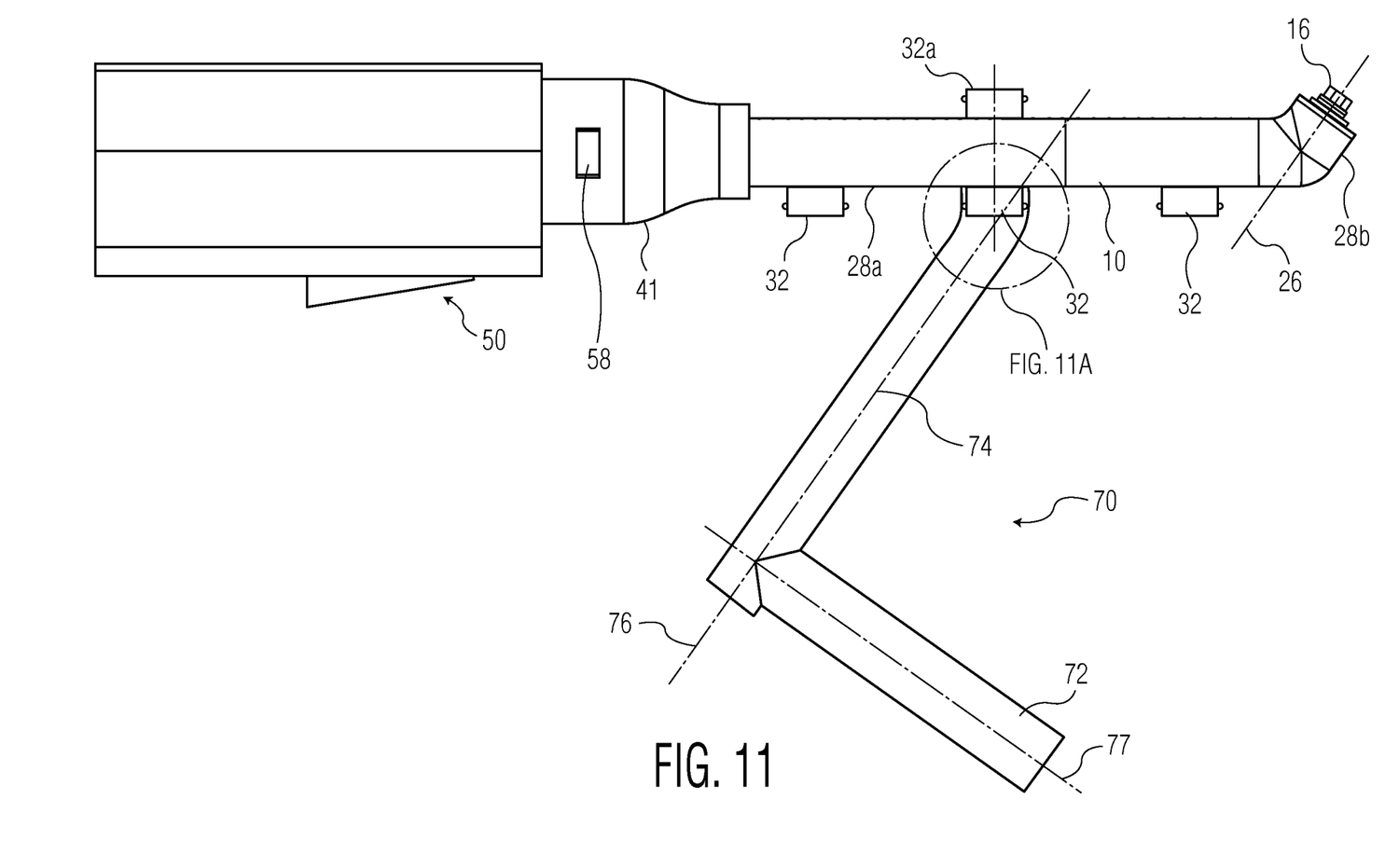
FIG. 11 is an assembly view of the drive housing of FIGS. 1-3, the sleeve of FIGS. 4-6, and the drive motor housing of FIGS. 7-10 including a modular handle arm mounted on the drive shaft housing.
Figure 11A:
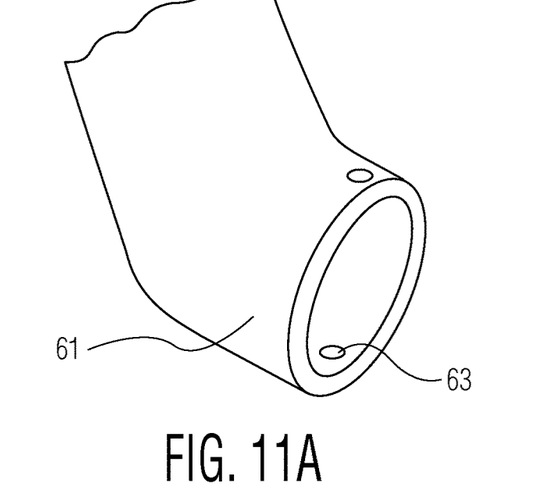
FIG. 11A is an isometric view of the modular arm for connection to the connector element of the reamer housing of FIG. 11.
Figure 12:
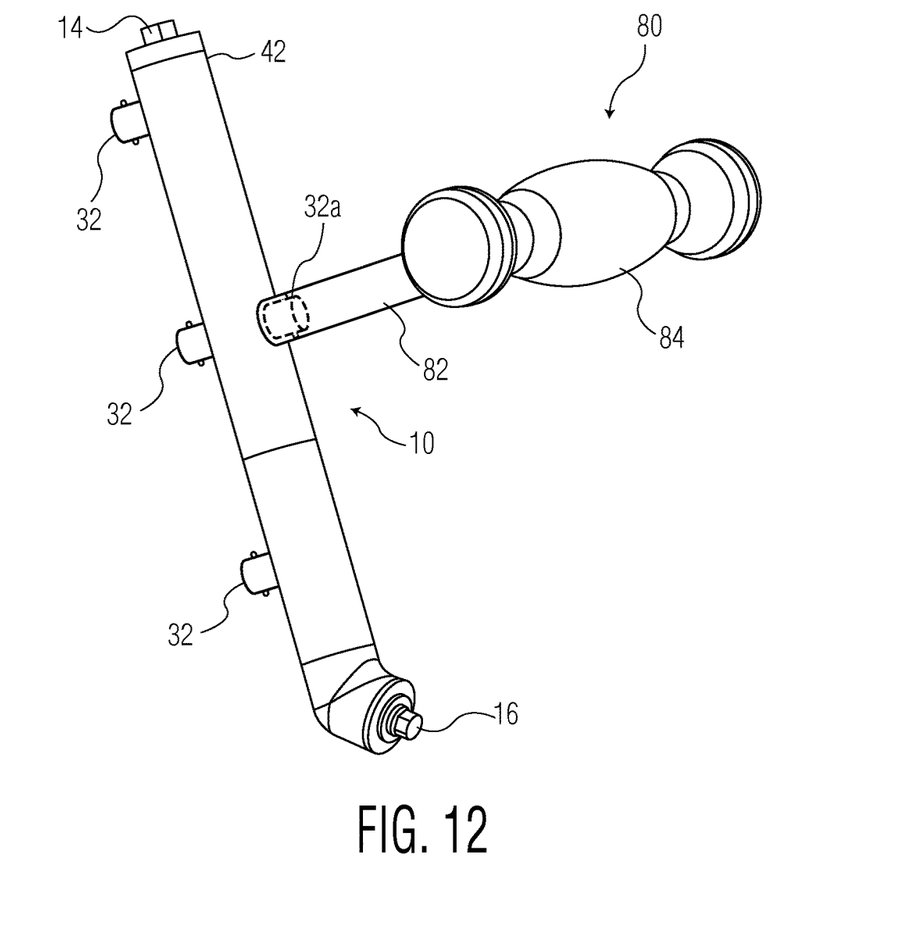
FIG. 12 is an isometric view of the drive system housing of FIGS. 1-3 including a t-shaped positioning handle mounted thereon.

Referring to FIGS. 11 and 11A there is shown an assembly of drive system 50, sleeve 41 and drive housing 28. Included on drive housing 28 is a handle 70 including a connector end 61 as shown in FIG. 11A. End 61 of handle 70 is connected to mounting portion 32a fixed to housing 28. End 61 may have a pair of through bores 63 for receiving the spring loaded detent pins 36 of mounting portion 32a. Preferably handle 70 includes a grip portion 72 and a connector arm portion 74 having an axis 76 oriented at right angles to an axis 77 of grip portion 72 which allows the surgeon to apply a force generally parallel to axis 26 of portion 28b. As shown in FIG. 11A end 61 is angled with respect to axis 76 so that connector arm portion 74 can be correctly aligned with axis 40. As can been seen in FIG. 11, an axis 76 of arm portion 74 is generally parallel to axis 26. Handle 70 can be placed on either of preferably three mounting locations 32 on the side of housing portion 28a opposite reamer head drive element 16. In addition, as shown in FIG. 12, a generally T-shaped handle 80 can be attached to a coupling element 32a by a shaft 82 having a hollow cylindrical end. Handle 80 has the same coupling end design as shown in FIG. 11A. Coupling element 32a for handle 80 is as shown in FIGS. 1A and 3A. Grip portion 84 of handle 80 may be of any ergonomic design.

Figure 13:
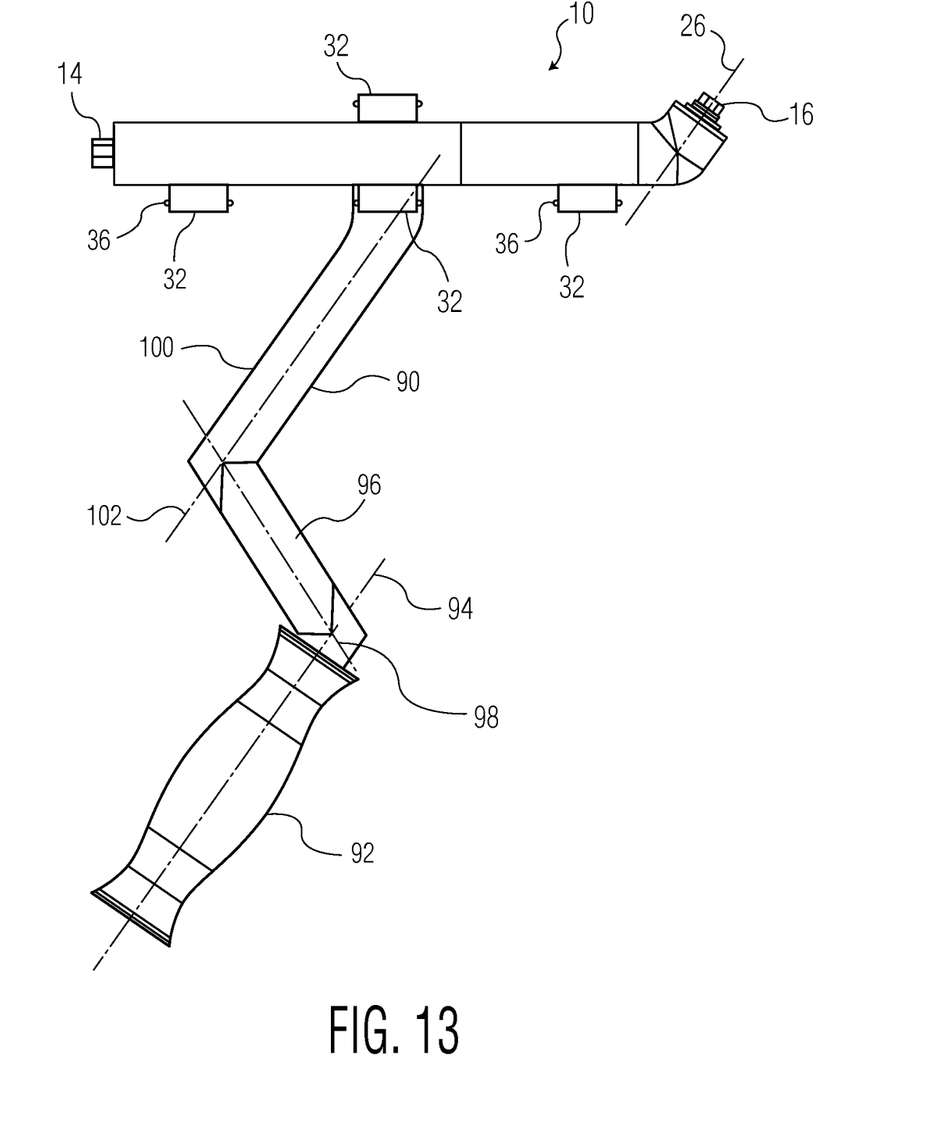
FIG. 13 is an elevation view of the drive system housing of FIGS. 1-3 including an alternate handle arm mounted thereon for applying a force along the axe of the angled reamer head drive system.

Referring to FIG. 13 there is shown an elevation view alternate handle 90 having a gripping portion 92 with an axis 94 coaxial or parallel to with axis 26 of drive element 16. Handle 90 has a second angled portion 96 along an axis 98 connected to a shaft portion 100 extending along an axis 102. Axis 94 forms an obtuse angle with axis 98 and with axis 102 with the lengths of handle portions 96 and 100 being selected to place the gripping portion outside the patient when the instrument 10 is being used to ream the acetabulum.

Figure 13A:
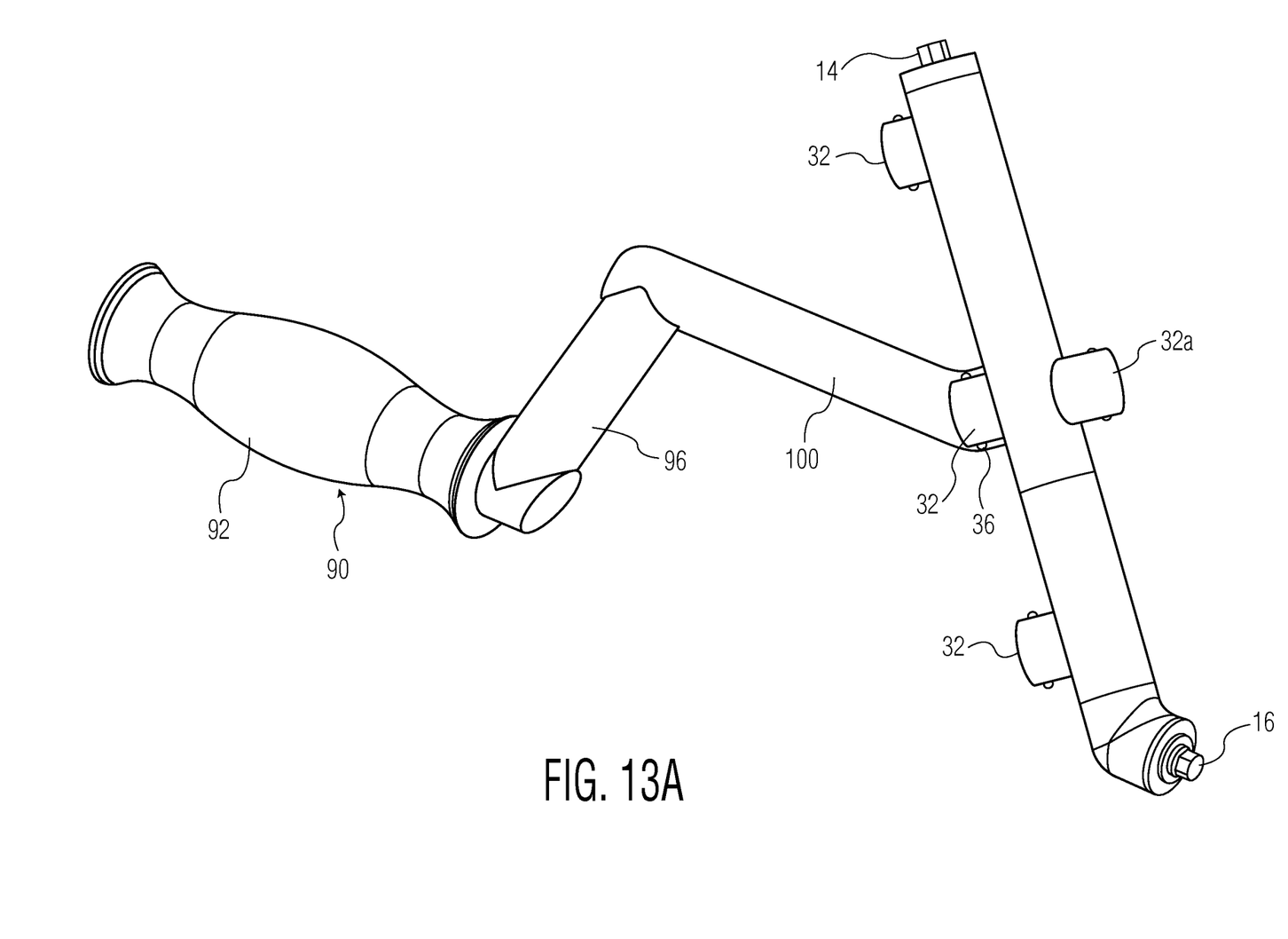
FIG. 13A is an isometric view of FIG. 13.
Figure 14:
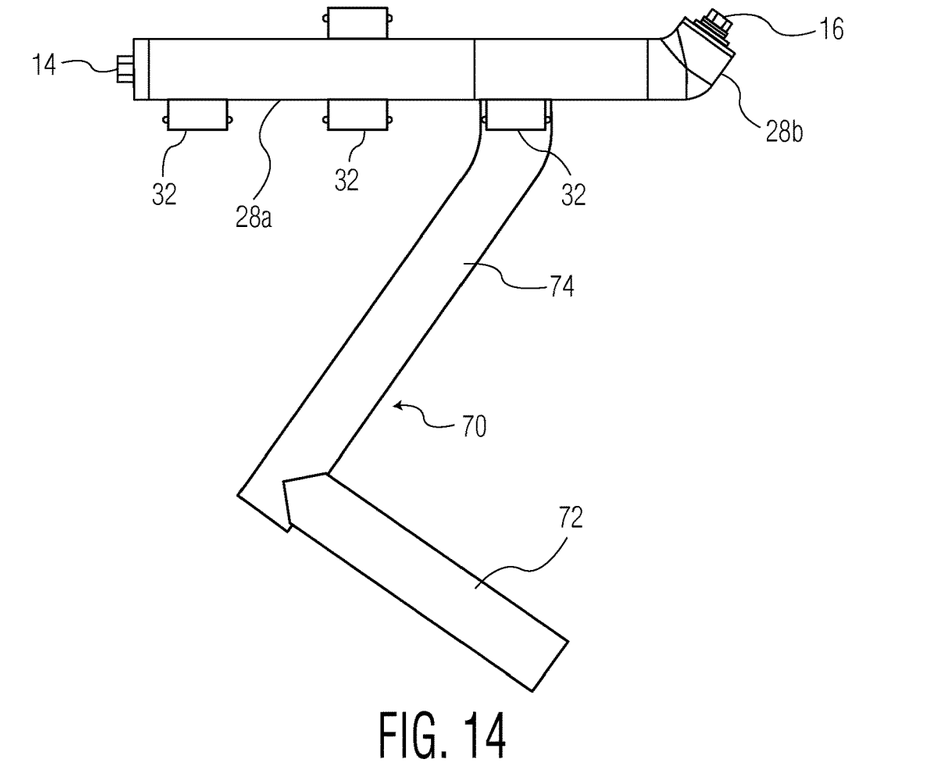
FIG. 14 shows the drive system housing as shown in FIG. 13 with the handle arm adapted to apply pressure or force in the direction of the head axis releasably mounted at a location closer to the reamer cutting head drive element.
Figure 14A:
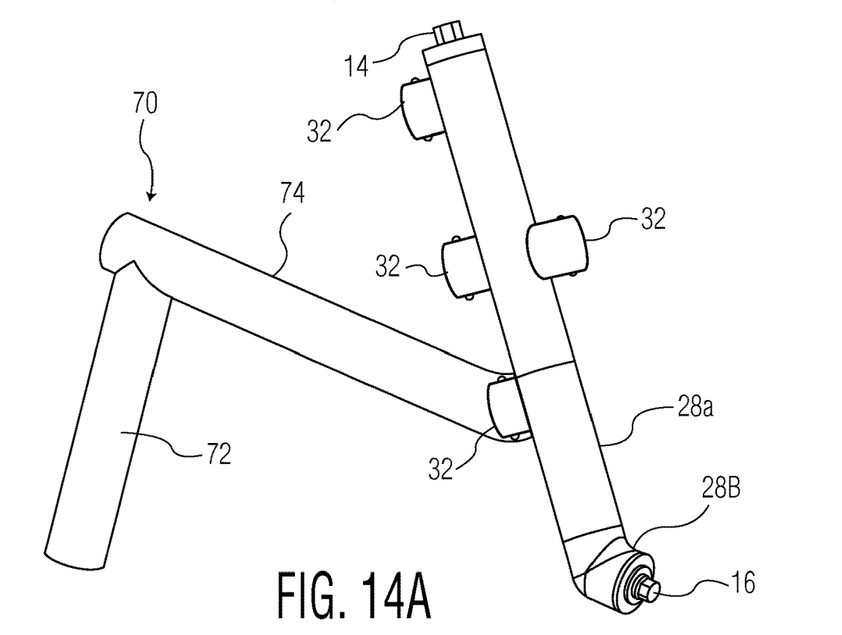
FIG. 14A is an isometric view in a rotated position of the drive system housing, handle and arm of FIG. 14.
Figure 15:
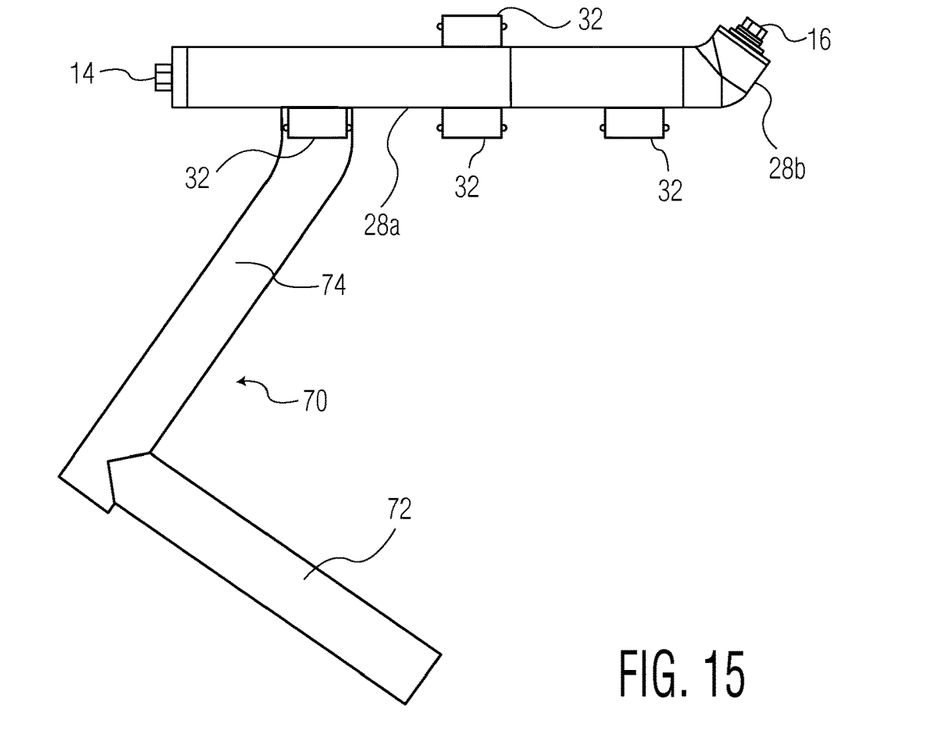
FIG. 15 is an elevation view of the drive system housing, handle and arm, with the handle located in a position further from the reamer cutting head drive element.
Figure 15A:
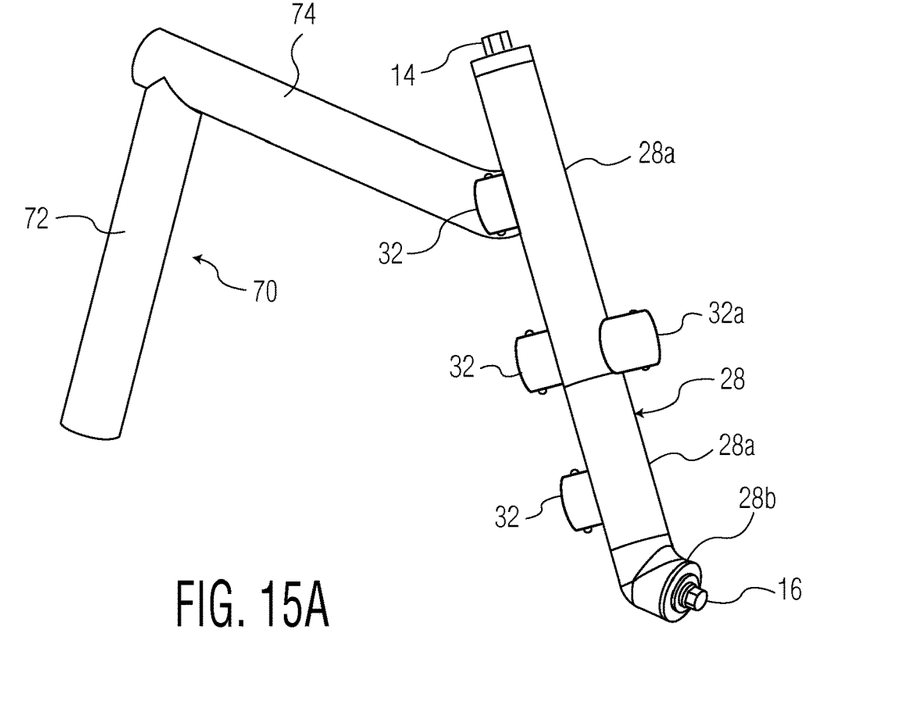
FIG. 15A is an isometric view of the drive system housing and handle rotated from that shown in FIG. 15.

FIG. 13A is an isometric view of the elevation view of FIG. 13 showing handle 90 mounted on the central connector element 32 including portions 96 and 100. FIGS. 14, 14A, 15 and 15A show a handle 70 connected respectively at the connecting element 32 which is closest to drive element 16, or connected to the connecting element 32 furthest from drive element 16. The selection of which of the preferably three connecting elements 32 on housing portion 28a depends on the anatomy of the patient whose acetabulum is being reamed. Obviously for a larger patient the connecting element 32 furthest from the drive element 16 would be utilized with handle 70. Furthermore, while handle 70 is shown, handle 90 could also be used to connect to any of the connecting elements 32.

Figure 16:
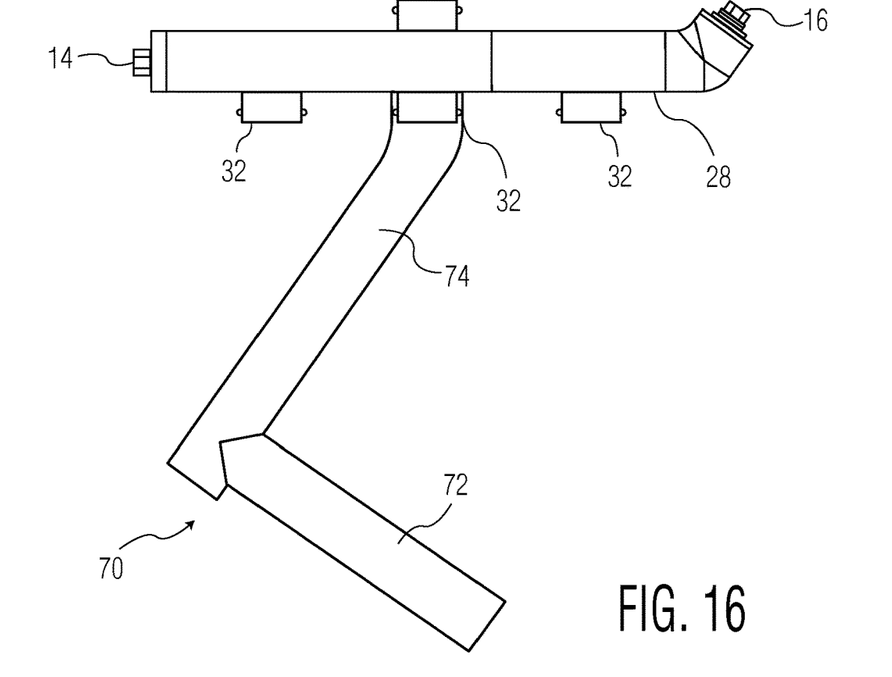
FIG. 16 is an elevation view of the drive system housing and handle arm with the handle, arm located in an intermediate position on the drive system housing.
Figure 16A:
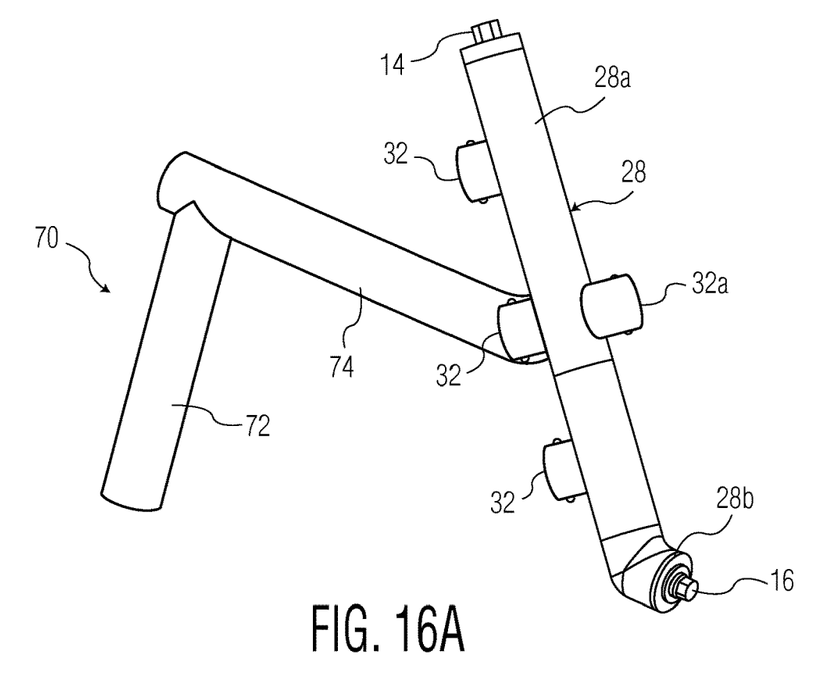
FIG. 16A is an isometric view of the handle, arm and drive system housing shown in FIG. 16.

FIGS. 16 and 16A are similar to FIG. 11, however, showing handle 70 connected to housing portion 28*a* via the central connecting element 32.

While drive system 50 is shown non-rotatably coupled to a housing 28 having a straight section 28A, the concept of the drive system being non-rotatably coupled to the housing 28 could be applied to a reamer having a curved or angled housing 28A. While connection or mounting elements 32, 32*a* are shown as modular, they could be permanently fixed to housing portion 28*a*. Also while four connecting elements 32 are shown inserted into four recesses 34, only one connecting element 32 or 32*a* is needed since it could be moved to any of the desired four recesses 34.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An acetabular reamer comprising:
a rotatable drive shaft extending along a first longitudinal central axis, the drive shaft having first and second ends;
a drive motor operatively coupled to the first end of the rotatable drive shaft for rotating the shaft;
a first housing enclosing the drive motor;
a second housing surrounding at least a first portion of the drive shaft, the second housing having a gripping portion;
a reamer cutting head rotatably coupled to the second end of the rotatable drive shaft, the reamer head rotatable about a second longitudinal central axis extending in a first direction at an acute angle with respect to the rotatable drive shaft first longitudinal central axis; and
a first releasable connector operatively coupling the first end of the rotatable drive shaft and the drive motor, a second releasable connector preventing relative rotation between the first housing and the second housing, and a third releasable connector coupling a second portion of the drive shaft and the reamer head,
wherein the second releasable connector is attached to the first housing at a first location on the second releasable connector and to the second housing at a second location on the second releasable connector, the second releasable connector being hollow with an inner diameter larger than an outer surface of the second housing,
wherein the first housing is the sole housing structure occupying a space interior to the inner diameter of the second releasable connector at the first location,
wherein the second housing is the sole housing structure occupying a space interior to the inner diameter of the second releasable connector at the second location, and
wherein the second releasable connector and a portion of the second housing abutting the second releasable connector are centered on the first longitudinal central axis.

2. The acetabular reamer as set forth in claim 1, wherein the second housing encloses the entire rotatable drive shaft.

3. The acetabular reamer as set forth in claim 2, wherein the drive motor is non-rotatably mounted in the first housing.

4. The acetabular reamer as set forth in claim 3, wherein the drive motor is either electric or pneumatic.

5. The acetabular reamer as set forth in claim 2, wherein the gripping portion of the second housing enclosing the drive shaft includes a mounting connector including an arm extending therefrom at a second acute angle relative to the second housing in a second direction opposite the first direction.

6. The acetabular reamer as set forth in claim 5, wherein the arm is modular and may be releasably coupled to the second housing.

7. The acetabular reamer as set forth in claim 6, wherein the second housing has at least two axially spaced mounting connector locations for receiving the arm.

8. The acetabular reamer as set forth in claim 7, wherein a second mounting connector location is spaced axially along the second housing at a greater distance from the reamer cutting head than the first location.

9. The acetabular reamer as set forth in claim 5, wherein the acute angle is 45°.

10. The acetabular reamer as set forth in claim 1, wherein the drive shaft has a first axially extending portion along the first longitudinal central axis and a second axially extending portion along the second longitudinal central axis, the first and second longitudinal central axes intersecting at the acute angle.

11. The acetabular reamer as set forth in claim 10, wherein the third releasable connector includes a universal joint coupling the rotatable drive shaft extending along the first longitudinal central axis to the reamer cutting head extending along the second longitudinal central axis.

12. The acetabular reamer as set forth in claim 10, wherein the acute angle is 45°.

13. An acetabular reamer comprising:
a first housing containing a drive motor system having an output shaft therein extending out of the first housing along a first longitudinal axis;
a reamer portion having a second housing having an acetabular reamer drive shaft therein, the second housing having a first end housing a first end of the acetabular reamer drive shaft releasably connected to the output shaft, the acetabular reamer drive shaft having a second end operatively coupled to an acetabular reamer cutting head;
a modular arm extending from the second housing and adapted to be releasably coupled to the second housing; and
a sleeve attached to the first housing and the second housing, the sleeve being hollow and having an inner diameter larger than an outer surface of the second housing,
the first and second housing having interlocking portions for coupling the drive motor system to the acetabular reamer drive shaft and for attachment to the sleeve to prevent relative rotation between the first and second housings, the acetabular reamer drive shaft and the output shaft having interlocking portions capable of transferring power from the output shaft to a reamer drive system to the acetabular reamer cutting head,
wherein the first housing is the sole housing structure occupying a space within the sleeve at a first location where the sleeve is attached to the first housing,
wherein the second housing is the sole housing structure occupying a space within the sleeve at a second location where the sleeve is attached to the second housing, wherein the second housing has a first attachment interface and a second attachment interface, and wherein the first attachment interface and the second attachment interface are both adapted for receipt of the modular arm, the second attachment interface being spaced axially relative to the first attachment interface along a second longitudinal axis of the second housing such that the second attachment interface is further from the acetabular reamer cutting head than the first attachment interface.

14. The acetabular reamer as set forth in claim 13, wherein the second housing encloses the entire rotatable acetabular reamer drive shaft.

15. The acetabular reamer as set forth in claim 14, wherein drive system comprises a drive motor connected to the acetabular drive shaft, the drive motor being mounted in the first housing.

16. The acetabular reamer as set forth in claim 13, wherein the first end of the acetabular reamer drive shaft extends in a first direction forming an acute angle with respect to the second end of the acetabular reamer drive shaft coupled to the acetabular reamer.

17. The acetabular reamer as set forth in claim 16, wherein the second housing includes a gripping portion formed adjacent the first end of the acetabular reamer drive shaft and the modular arm extends from the second housing at a second acute angle relative to the second housing in a second direction opposite the first direction.

18. The acetabular reamer as set forth in claim 17, wherein the acute angle is 45°.

19. The acetabular reamer as set forth in claim 13, wherein the acetabular reamer drive shaft has a first axially extending portion along the second longitudinal axis and a second axially extending portion along a third longitudinal axis, the second and third longitudinal axis intersecting at an acute angle.

20. The acetabular reamer as set forth in claim 19, wherein a connector including a universal joint couple the first axially extending portion of the acetabular reamer drive shaft to the second axially extending portion of the acetabular reamer drive shaft.

21. The acetabular reamer as set forth in claim 13, wherein the drive motor is either electric or pneumatic.

22. The acetabular reamer as set forth in claim 13, wherein the first longitudinal axis and the second longitudinal axis are coincident.

23. The acetabular reamer as set forth in claim 13, wherein the first longitudinal axis and the second longitudinal axis are not coincident.

\* \* \* \* \*